United States Patent
Viscomi et al.

(10) Patent No.: US 8,136,194 B2
(45) Date of Patent: Mar. 20, 2012

(54) DISPOSABLE FINGER MOUNTED INSTRUMENT CLEANER

(76) Inventors: Brian D. Viscomi, Easton, PA (US); Dominic Anthony Viscomi, Easton, PA (US); Julie Glazer, Paramus, NJ (US)

( * ) Notice: Subject to any disclaimer, the term of this patent is extended or adjusted under 35 U.S.C. 154(b) by 939 days.

(21) Appl. No.: 11/726,332

(22) Filed: Mar. 21, 2007

(65) Prior Publication Data

US 2007/0283515 A1    Dec. 13, 2007

Related U.S. Application Data

(60) Provisional application No. 60/813,025, filed on Jun. 13, 2006.

(51) Int. Cl.
*B08B 1/00* (2006.01)
*A61C 3/00* (2006.01)

(52) U.S. Cl. .................. 15/104.92; 15/167.3; 206/63.5; 224/218; 433/49; 433/163

(58) Field of Classification Search ............... 15/104.92, 15/104.94, 167.3; 224/218; 433/49, 163; 206/163.5; *A61C 3/00*
See application file for complete search history.

(56) References Cited

U.S. PATENT DOCUMENTS

| | | | |
|---|---|---|---|
| 4,844,308 A * | 7/1989 | Porteous | 224/217 |
| 5,368,482 A | 11/1994 | Johnsen et al. | |
| 6,036,490 A | 3/2000 | Johnsen et al. | |
| 6,257,888 B1 * | 7/2001 | Barham | 433/163 |
| 6,971,879 B2 * | 12/2005 | Discko, Jr. | 433/163 |
| 6,986,924 B2 * | 1/2006 | Croll | 428/40.1 |
| 7,014,463 B2 | 3/2006 | Savola | |
| 2006/0166170 A1 * | 7/2006 | Masters | 433/215 |

* cited by examiner

Primary Examiner — David Redding

(57) ABSTRACT

A disposable finger mounted instrument cleaner (2) of the type having a semi-circumferential protective body (4) with a swiping expanse (6) to generously occlude lateral and extensor aspects of a finger and a tapered gripping coil (10) to wrap around the flexor aspects of a finger. Attached to the swiping expanse is an adherent foam body (14) with a number of pressure sensitive grooves (18) and debris traps (16) so that an instrument can be inserted into the pressure grooves to deposit debris in the debris traps. In Addition, the foam body has a pocket (20) for thorough instrument immersion and for holding desired medicaments.

7 Claims, 13 Drawing Sheets

DISPOSABLE FINGER MOUNTED INSTRUMENT CLEANER

CROSS REFERENCE TO RELATED APPLICATIONS

This application claims the benefit of Provisional Patent Application Ser. No. 60/813,025, Filed Jun. 13, 2006 by the present inventors

FEDERALLY SPONSORED RESEARCH

Not Applicable

SEQUENCE LISTING OR PROGRAM

Not Applicable

BACKGROUND

1. Field of Invention

This invention applies to the fields of Dentistry and Medicine in particular to allow for the ergonomic cleaning of and application of medications and or disinfectants to operative hand instruments in a protective manner concurrent with performing a procedure.

2. Prior Art

Dentistry and its medical counterpart may avail of this invention's novelty regarding chair-side procedures, and specifically those procedures which require the close proximity of both hands. In Dentistry, typically during the scaling phase of a dental prophylaxis, the Hygienist will retain a cleaning cloth (gauze sponge) within the fingers of the hand opposite that of the one employing the instrument. When not cleaning the instrument head, these fingers often times are in use to hold an auxiliary instrument or to retract oral structures (cheek, tongue, lips). To clean the debris laden (blood and calculus) instrument, the operator must make a deliberate hand (rotation) and fingers (compression of the instrument working end within the confines of the gauze sponge) adjustment. This maneuver among other things causes a disruption during the procedure with constant hand repositioning and interrupts the usage of that hand. Also the instrument potentially can be wiped by an area in the gauze previously laden with contaminated bacterial debris with the likelihood of reintroducing pathogens back into the periodontal structures (gums). There is also opportunity to experience an inadvertent self-induced instrument stick with its subsequent unwanted sequelae. The fingers-holding gauze technique also precludes the instrument holding ability of that hand. Although this scenario represents the standard protocol in a typical dental prophylaxis procedure, there does exist alternative ways to by-pass the fingers and gauze technique.

U.S. Pat. No. 4,844,308 to Porteous, Don D., Jul. 4, 1989 presents a finger mounted cup designed to hold dental paste or tooth cleaning agent. It permits an instrument to access and procure its contents but does not provide for instrument cleaning and debridement.

U.S. Pat. No. 5,368,482 to Johnsen, James B., Nov. 29, 1994 presents a finger mounted dental instrument servicing system for instrument cleaning and to transfer a medicament to an operative site. It is composed of disposable and non disposable components. Its myriad of components i.e. wiping sponge, appendage to hold cleaning medicaments and root canal file measuring scale can present the operator with ergonomic challenges. Furthermore, the components rest upon a horizontal platform which dictates an optimal position on the operator's finger in order to be most accessible. The instrument cleaning sponge presents a homogenous surface which can impede instrument insertion and withdrawal. The non disposable component also presents with cleaning and sterilization considerations.

U.S. Pat. No. 6,257,888 to Barham, William L., Jul. 10, 2001 presents as an instrument cleaning device and a separate polish dispensing receptacle. This device is adhesively secured to back of the hand which necessitates deliberate hand rotation to access and does not permit aggressive engagement of the instrument head to remove stubborn debris.

U.S. Pat. No. 6,036,490 to Johnsen, James B., Mar. 14, 2000 also presents as a dental instrument servicing device. However, the application for this device is intended for Endodontic (root canal) therapy. Its plurality of components precludes its practicality for non-endodontic procedures.

U.S. Pat. No. 6,971,879 to Discko, John J. Jr., Dec. 6, 2005 claims a material dispensing instrument cleaning sponge. This sponge presents with a singular slit and an adhesive backing as a preferred means of attaching to the hand. Hence, relocation or adjusting may compromise the sponge's integrity and or cause unwanted expression of the sponge's fluid contents. Also, to avail of multiple cleaning grooves it is necessary to affix additional sponges to the hand. Furthermore this device promotes itself for delivery exclusively for low viscosity agents, precluding its ability to contend with those of a highly viscous nature.

U.S. Pat. No. 6,986,924 to Croll, Theodore P., Jan. 17, 2006 presents a semi-rigid adhesively attached finger mounted receptacle to facilitate the delivery of pastes and solution and does not function in the capacity of instrument debridement or finger protection.

U.S. Pat. No. 7,014,463 to Savola, Dominic, Mar. 21, 2006 presents as a device which relies on a circular tuft of bristles to engage and debride instrument heads. It doe not purport to retain or dispense pastes or medicaments. Furthermore it does not allow for instrument decontamination.

Accordingly, several advantages of the present patent application of Brian D. Viscomi, Dominic A. Viscomi, and Julie A. Glazer for "DISPOSABLE FINGER MOUNTED INSTRUMENT CLEANER" are:

(a) Anatomically contoured to conform to individual's finger shape and size (b) Provides circumferential work field close to operative field (c) Circumferential design provides for greater surface area (d) Guards against accidental finger stick (e) Fluted design permits instrument's ease of insertion into cleaning groove (f) Fluted design frictionally engages instrument to ensure removal of debris (g) Multiple grooves make for more efficient use of sponge surface (h) Cleans and disinfects working end of instrument (i) Provides as a vehicle for introducing medicated solutions into the operative area (j) Can provide for the introduction of topical anesthetic to the operative site (k) Ergonomic placement and design promotes efficiency and lessens hand fatigue (l) Esthetic streamlined appearance (m) One size fits all and is disposable

SUMMARY OF THE INVENTION

It is thus the object of this invention to provide a disposable, generally circumferential finger mounted dental or medical chair-side instrument cleaning device.

It is the further aim of this invention to disinfect the instrument's operative end during the process.

This invention also allows for multiple grooved channels on a singular body that provide ergonomic ingress and egress of the instrument head Another object of this invention is to provide additional protection to the operator against inadvertent instrument sticks.

Accordingly, a finger mounted device which can be impregnated with an appropriate solution to clean and disinfect an operative instrument in a protected manner while allowing the clinician to function with minimal disruption of hand movements during the operative procedure.

DRAWINGS

Figures

DRAWINGS

Reference Numerals 2. finger mounted instrument cleaner
4. protective ring
6. swiping expanse
8. gripping grooves
10. gripping coil
12. flexion termination
14. foam body
16. debris trap
18. pressure groove
20. pocket
22. pocket cover
24. adhesive substrate
26. adhesive sheath
28. enclosed debris trap
30. medial division
32 securing strap
34. strap adhesive
36. Instrument deflection guard
38. pocket guard
40. truncated recessed debris trap
42. contoured pressure groove
44. operator
46. instrument
48. instrument head
50. debris
52. swiping process
54 trapped debris
56 pocket insertion
58. medicament

DETAILED DESCRIPTION

FIGS. 1A, 1B, 1C, 1D, 1E—Preferred Embodiment

Figure 1A:
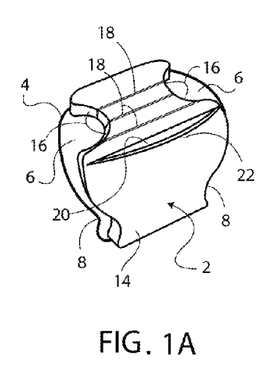
FIGS. 1A-1E show various views of the preferred embodiment for the finger mounted instrument swipe.
Figure 1B:
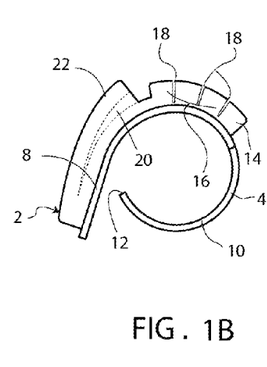
Figure 1C:
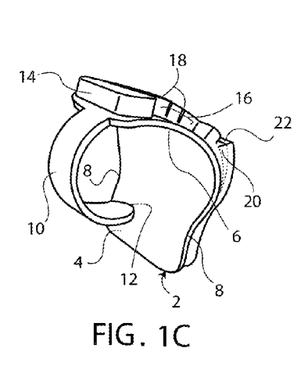
Figure 1D:
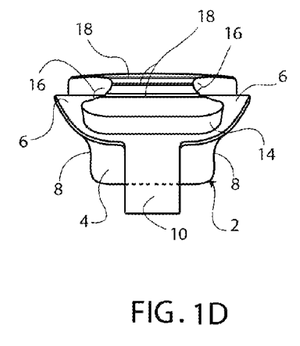
Figure 1E:
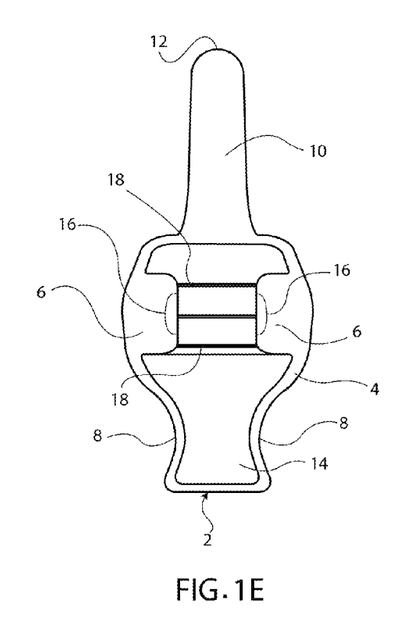

FIG. 1A shows a frontal three-quarter view of the preferred embodiment. FIG. 1B shows a side view. FIG. 1C shows a rear three-quarter view. FIG. 1D shows a back view. FIG. 1E shows an uncoiled (flattened) plane view of the preferred embodiment.

Figure 3:
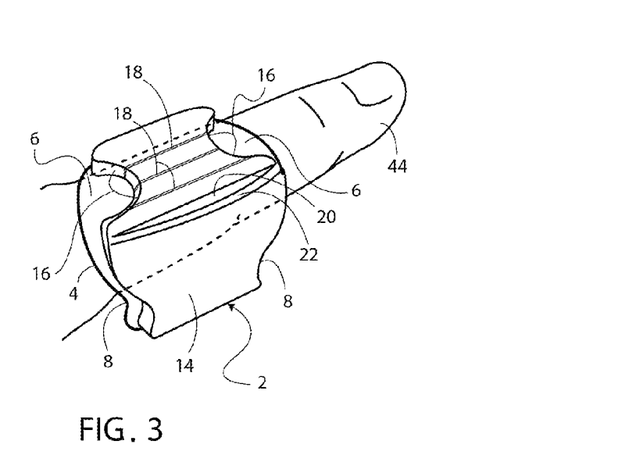
FIG. 3 shows a disposable instrument cleaner on a finger.

The finger mounted instrument cleaner 2 consists of a hardened semi-cylindrical shell or protective ring 4 with a compressible foam body 14 attached to it. The ring 4 is mostly circumferential, and has a somewhat hourglass shaped flared region. This flared region or swiping expanse 6 is ergonomically sized to correlate with and generously occlude the extensor and lateral aspects of finger while worn (FIG. 3). Ideally, during wear, the expanse 6 extends from a knuckle to a distance just beyond the first phalange joint (FIG. 3). Located on the inferior lateral periphery of the swiping expanse 6 is a gentle constricting taper consisting of two contours. These contours, concavities or gripping grooves 8 are laterally positioned formations in the swiping expanse's 6 lower periphery. While worn, the grooves 8 permit an interlocking engagement with a flexed finger (not shown). The lateral distance between these grooves 8 is wide enough to encourage minimal gripping effort during finger/groove 8 interlocking while maximizing swipe stability.

Figure 4:
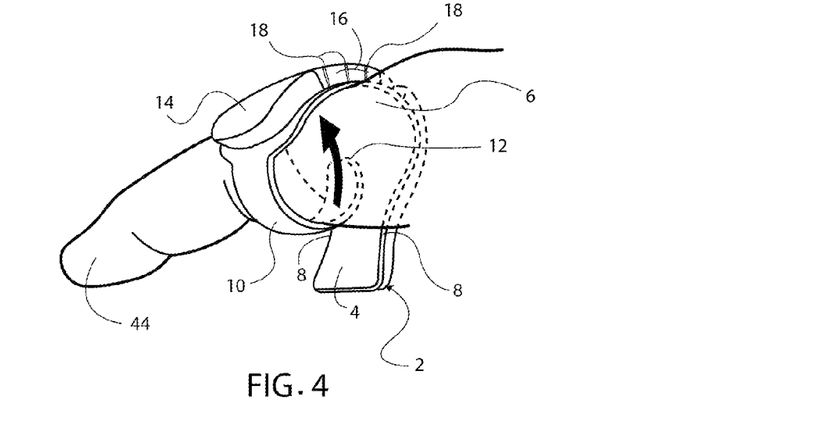
FIG. 4 shows the gripping coil wrapped around the flexor aspect of an operator's finger.
Figure 5:
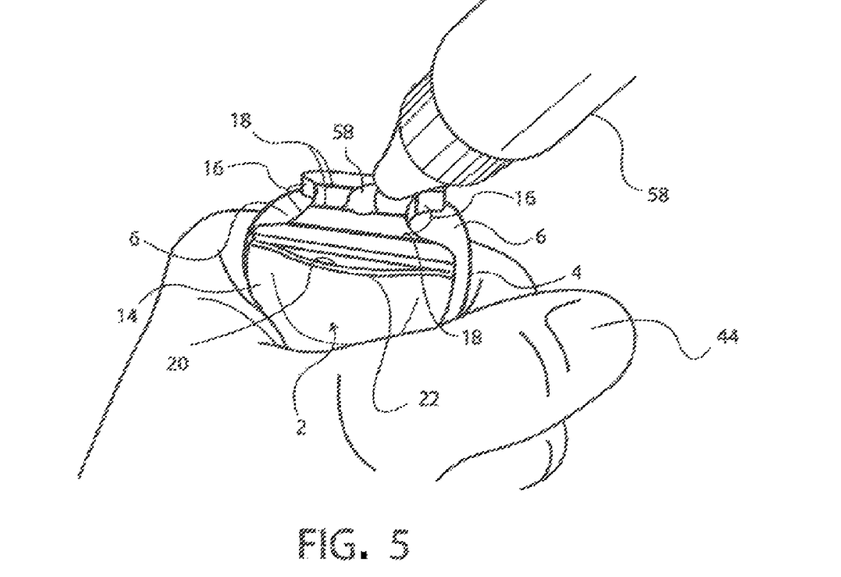
FIG. 5 shows medicaments being applied to pressure grooves.

Originating from the superior termination or upper edge of the swiping expanse 6 is an acutely tapered continuous curved extension or gripping coil 10. The gripping coil 10 is partially circumferential and extends from the superior swiping expanse's edge 6 to underneath the lower portion swiping expanse 6 (In the vicinity of the gripping grooves). The coil's 10 acute taper is designed to wrap around and correlate with the lateral and flexor portions of a finger while worn (FIG. 4). The coil 10 has a non-connective termination or flexion termination 12. The termination 12 non-connective nature adjustably accommodates an array of inserted volume variances.

Adhering to the expanse's 6 face is a broadly covering, semi-dense compressible layer or foam body 14. The foam body 14 has a mostly similar but slightly smaller dimension than that of the swiping expanse 6. Formed into the upper periphery of the foam body 14 are two lateral insets, lagoon like inlets or debris traps 16. Contained within the area of the debris traps 16 are numerous horizontal interfaces, slits, or pressure grooves 18 (FIG. 1A). These grooves 18 run horizontally across its face connecting the two lateral debris traps 16. The grooves 18 are of a sufficient depth to allow for enveloping the inserted of a variety of medical instrument heads. Although there are three grooves pictured in this preferred embodiment, any number of additional grooves may be formed into the foam body 14 surface. Note, the inset trap 16 design exposes a substantial potion of the protective ring's 4 swiping expanse 6. This exposed expanse 6 of hardened material promotes protective instrument contact with the swiping expanse 6 during instrument insertion into a groove 18.

Located a short distance below the pressure grooves 18 is a pouch or pocket 20. The pocket 20 is an opening much greater volume and possesses greater insertion potential than the superiorly positioned pressure grooves 18. The pocket exterior or expansive pocket cover 22 expansively opens, permitting for total instrument head immersion FIGS. (1A and 1C).

The finger mounted instrument swipe 2 can be made from any number of materials. The protective ring 4 may be made from any material that is sufficiently puncture resistant. Synthetics such as plastics are preferred although natural materials and any number of metals/alloys may be utilized. The protective body 2 can be injection molded or die stamped from planar sheet stock and thermally shaped into configuration. The foam body 14 may be fabricated from open or closed cell synthetic foams or any other suitable natural compressible material. The foam body 14 may be fabricated from one piece or may be formed by layering sheets of foam upon each other. The foam body 14 may then be adhesively attached to the ring's 4 swiping expanse 6. The grooves 18 and pocket 20 may be made from injection molding. Lastly, Finger Mounted Instrument Cleaner 2 can be fabricated with a singular injection mold as one piece.

FIGS. 14-23

Alternative Embodiments

Figure 14A:
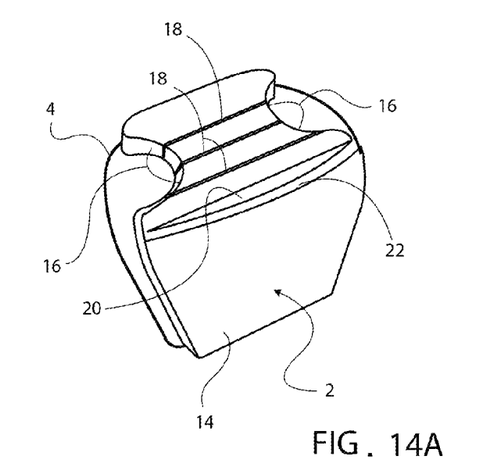
FIGS. 14A-14C show various views of an alternative embodiment with an adhesive substrate.
Figure 14B:
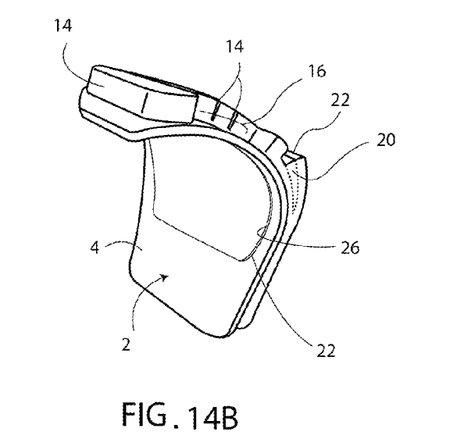
Figure 14C:
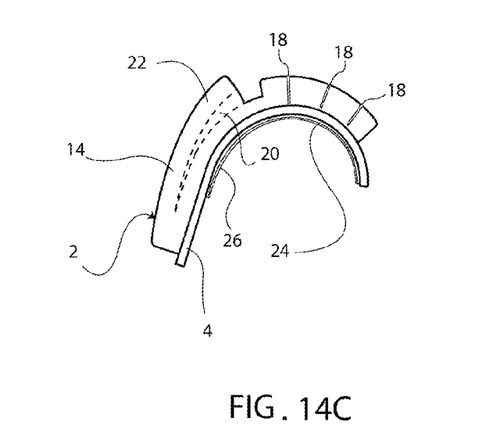
Figure 15:
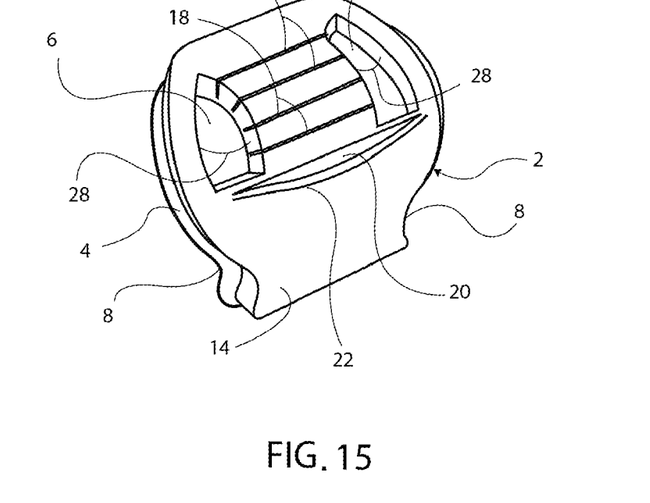
FIG. 15 shows a dimensional view of an instrument cleaner with enclosed debris traps.
Figure 16:
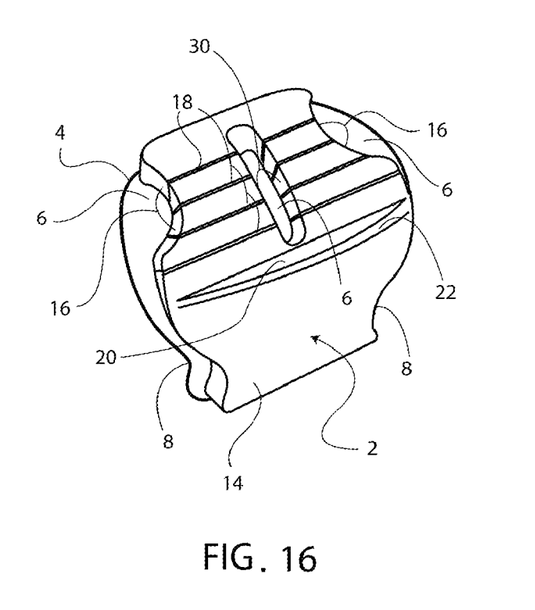
FIG. 16 shows a dimensional view of an instrument cleaner with a medial division debris trap.
Figure 17A:
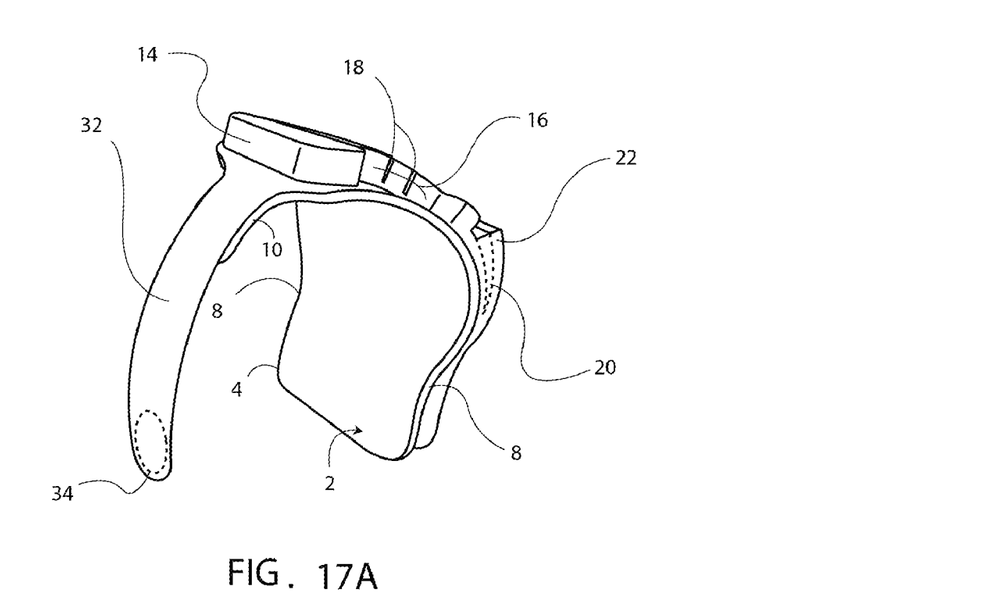
FIGS. 17A and 17B show various views of a disposable instrument cleaner with a securing strap.
Figure 17B:
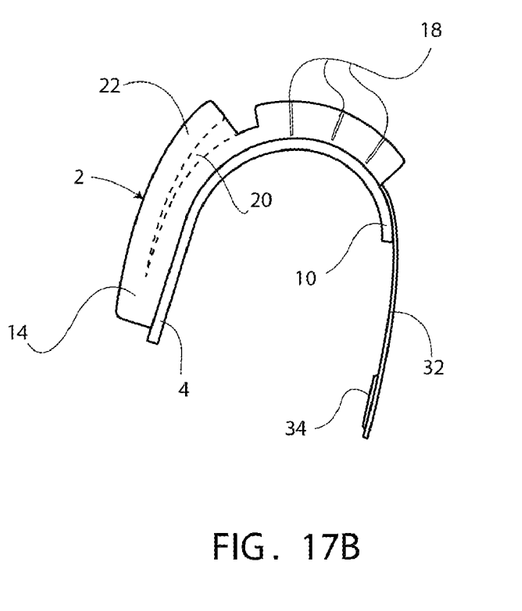
Figure 18:
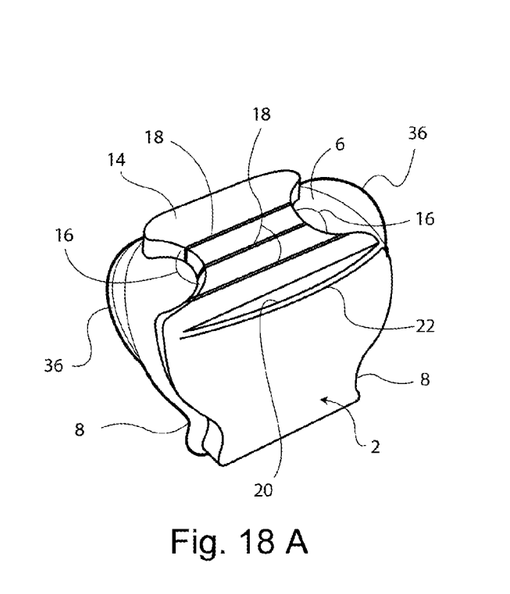
FIGS. 18A-18C show various views of an instrument cleaner with flared instrument deflection guards.
Figure 19:
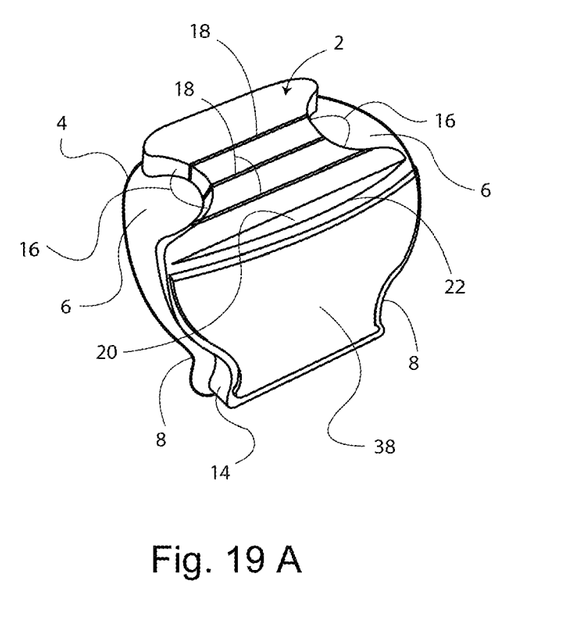
FIGS. 19A and 19B show various views of an instrument cleaner with an applied pocket guard.
Figure 20A:
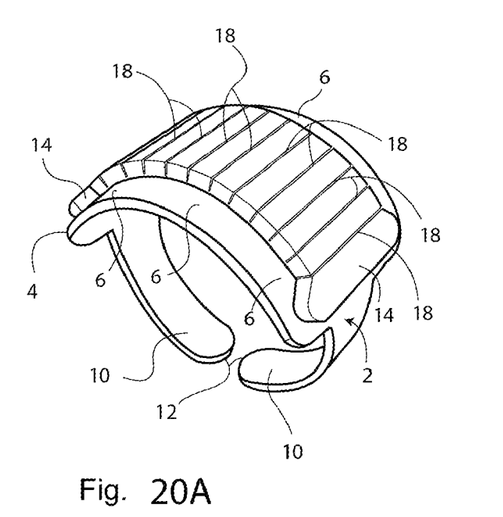
FIGS. 20A and 20B show various views of an instrument cleaner with a symmetrical construction, two gripping coils and no pocket.
Figure 20B:
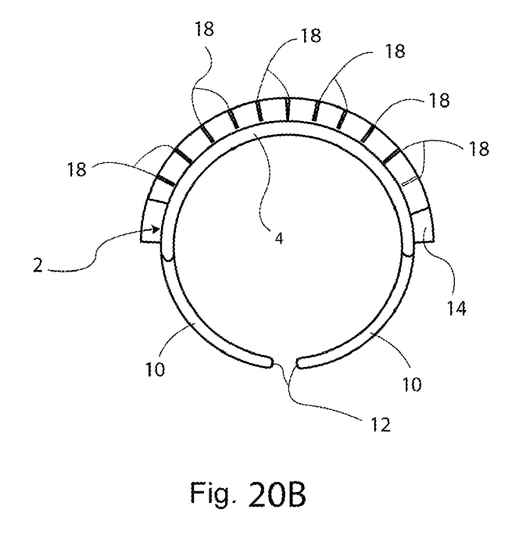
Figure 21:
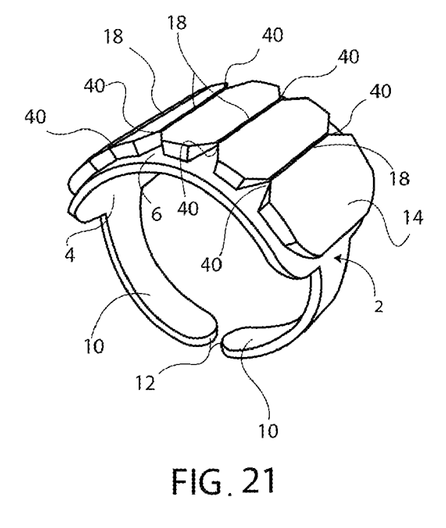
FIG. 21 shows an instrument cleaner with a number of truncated recessed debris traps.
Figure 22:
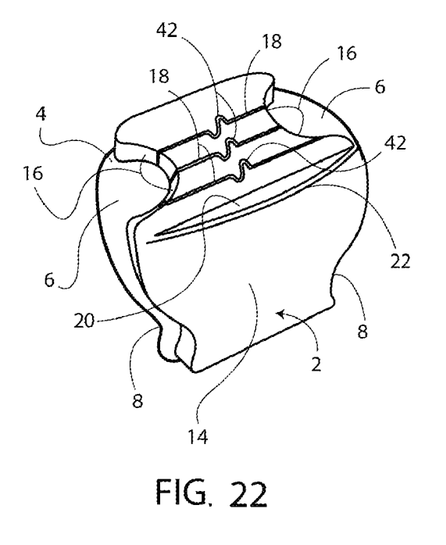
FIG. 22 shows an instrument cleaner with contoured pressure grooves.
Figure 23:
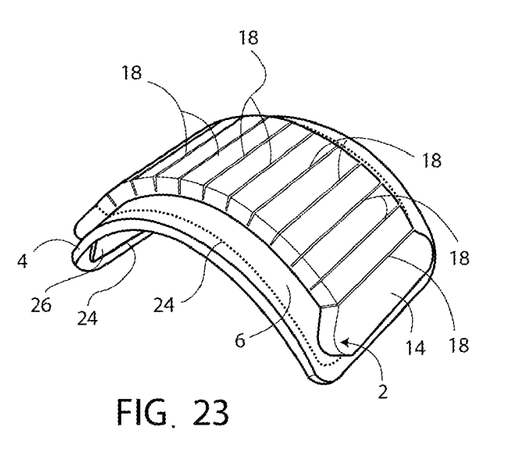
FIG. 23 shows a simplified instrument cleaner with an adhesive substrate, no gripping coil, and no pocket.

There are many possibilities for the finger mounted cleaner 2 with regard to configurations of the protective body 4, foam body 14 and means for attachment to a finger. In FIGS. 14A-14C, the finger mounted instrument cleaner features an adhesive film or substrate 24 covered by a peel-able adhesive sheath 26. FIG. 15 shows an instrument cleaner 2 with two enclosed debris traps 28. FIG. 16 shows a cleaner 2 with a centrally positioned medial division 30 debris trap. FIGS. 17A and 17B show a cleaner 2 with a securing strap 32. The securing strap 32 has an area of strap adhesive 34 for fastening. FIGS. 18A-18C show a cleaner 2 with two flared instrument deflection guards 36 that flare up from the protective body 4. FIGS. 19A-19B show various views of a cleaner 2 with a pocket guard 38 applied to the exterior of the pocket cover 22. FIG. 20A-20B show a cleaner 2 with mirrored gripping coils 10, extended debris traps 16 and no pocket 20. FIG. 21 shows a cleaner 2 with multiple truncated recessed debris traps 40. The traps 40 are beveled to entrap debris under the foam body upon instrument insertion. FIG. 22 shows a cleaner 2 with contoured pressure grooves 42. FIG. 23 shows simplified cleaner 2 with an adhesive substrate 24, no swiping pocket 20 and no gripping coils 10.

Operation—FIGS. 2-12

Figure 2:
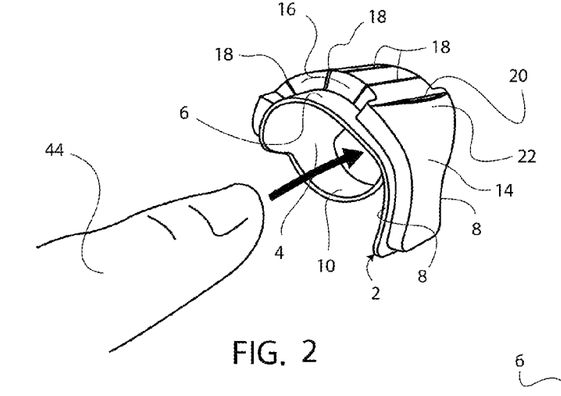
FIG. 2 shows an operator's finger being inserted into an instrument cleaner.
Figure 6:
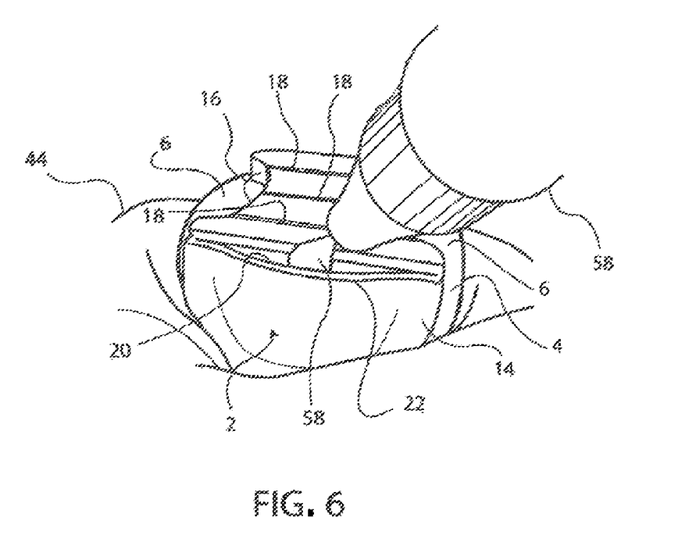
FIG. 6 shows medicaments being applied inside the instrument cleaner's pocket.

To use the finger mounted instrument cleaner 2, an operator 44 first orients the cleaner 2 to place on a desired finger. To orient the cleaner 2, the swiping expanse 4 and foam body 14 portions are positioned to correlate with the extensor and lateral aspects of an operator's 44 finger (FIG. 2). This will permit unobstructed ergonomic access with instrumentation. Next, the cleaner 2 is placed on the operators 44 finger. When properly placed, the lateral and extensor portions of the operator's 44 finger are generously occluded by the swiping expanse 6 and foam body 14 portions of the swipe 2 (FIG. 3). Additionally, the gripping coil 10 wraps snugly around the lateral and flexor portions of an operator's 44 finger (FIG. 4). Next, the operator 44 flexes a finger to engage the gripping grooves 8. Groove 8 flexion can be moderated by the operator 44 when needed to permit the cleaner's adjustment on the finger as well as promote stability for debriding an instrument. Optionally, before a procedure, the operator 44 can apply any number of desired medicaments 58 to the grooves 18 (FIG. 5) or pocket 20 interior (FIG. 6).

Figure 7:
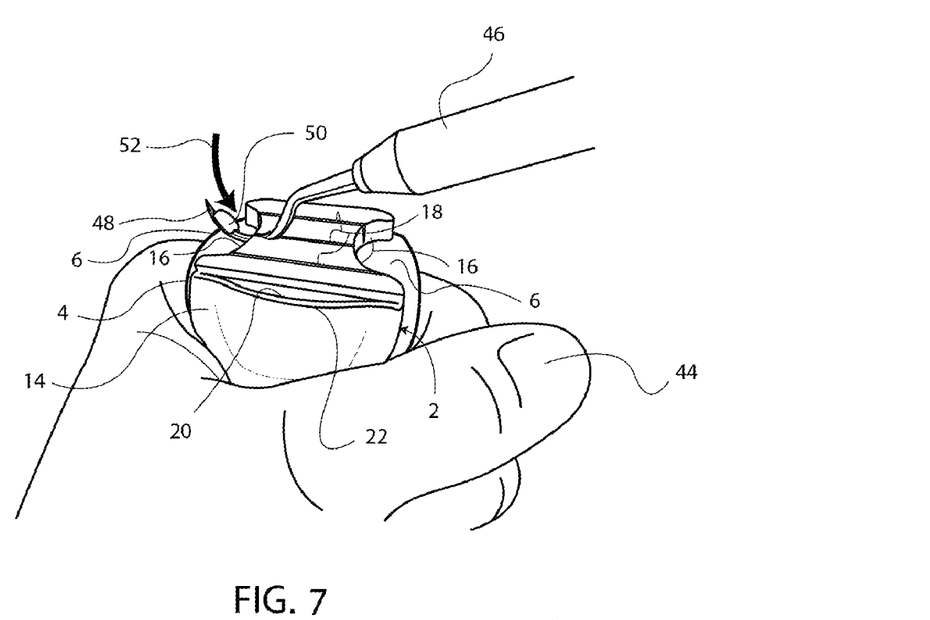
FIG. 7 shows an instrument with accumulated debris being inserted into a pressure groove via a debris trap.
Figure 8:
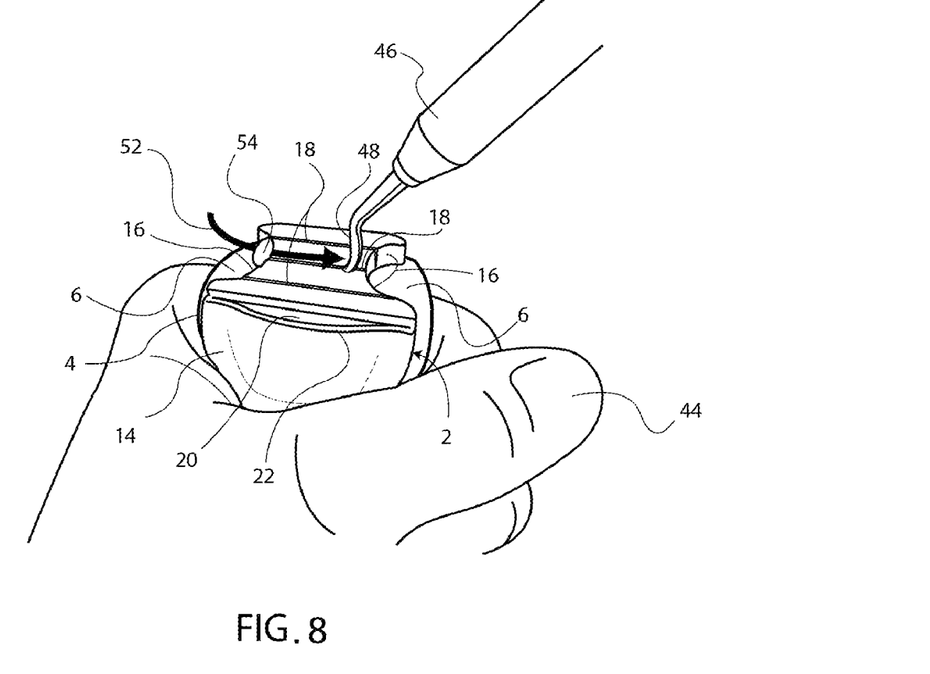
FIG. 8 shows an instrument being swiped through a pressure groove, entrapping debris in a debris trap.
Figure 9:
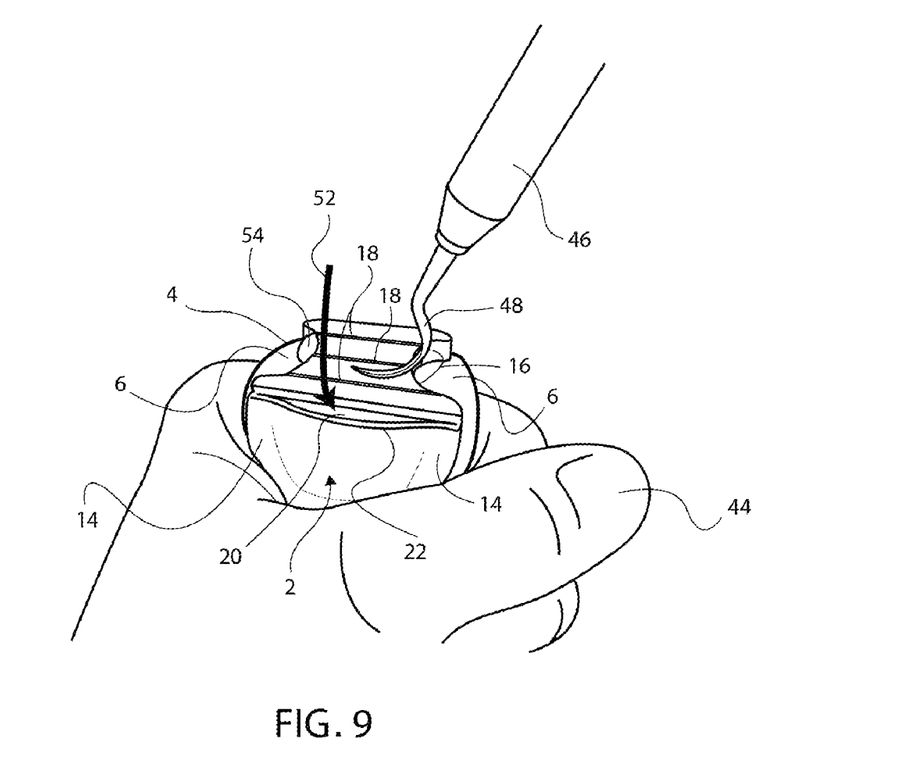
FIG. 9 shows an instrument head being inserted into the pocket.
Figure 10:
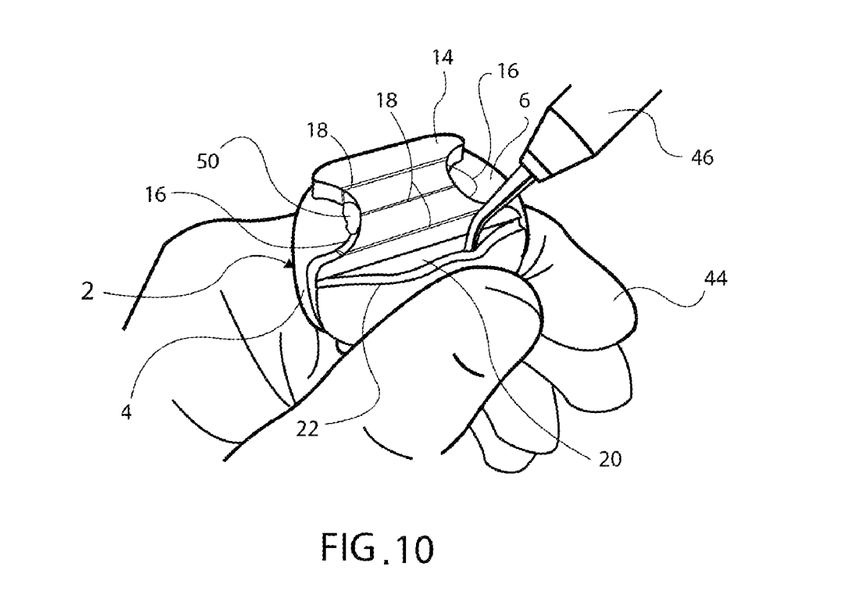
FIG. 10 shows the instrument head enveloped in the pocket.
Figure 11:
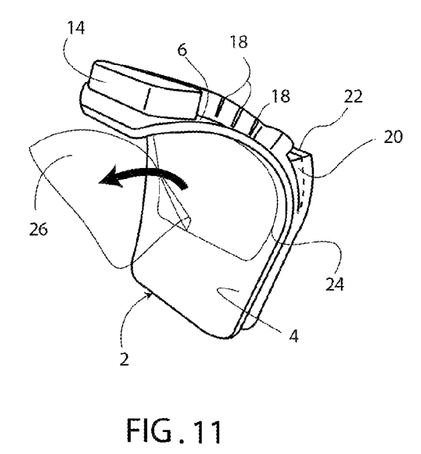
FIG. 11 shows a disposable instrument cleaner with an adhesive sheath being removed.
Figure 12:
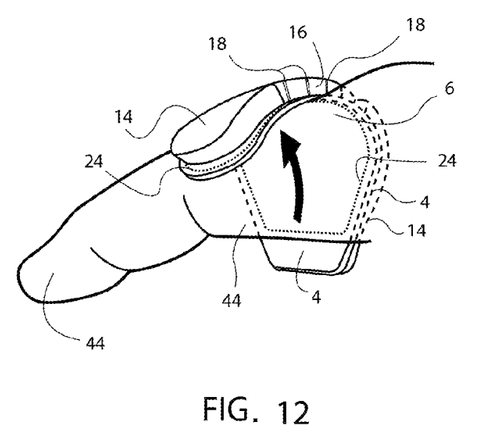
FIG. 12 shows a disposable instrument cleaner adhesively attached to a finger.

Next, during an operative procedure, debris 50 accumulates on the instrument 46. As needed, the instrument 46 is then directed into one the debris traps 16 to engage a pressure groove 18 (FIG. 7). This begins the swiping process 52. As the instrument 46 engages and enters the groove 18, the surrounding foam body 14 envelops the instrument head 48. As the instrument head 48 is swiped 52 through the groove 18, the accumulated debris 50 is removed and deposited in the debris trap 16 (FIG. 8). This debris 50 is now trapped debris 54. Next, the instrument 46 is inserted into the pocket 20 for further cleaning, sterilizing or to access medicaments 58. The swiping process 52 is then repeated as necessary using any number of grooves 18 as trapped debris 54 accumulates within the cleaner's 2 traps 16.

Figure 13:
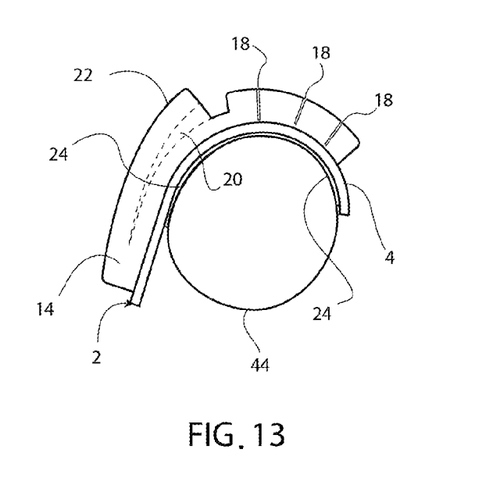
FIG. 13 shows a side view of a disposable instrument cleaner adhesively attached to a finger.

Note (FIGS. 11-13) show an alternative method to attach to a finger using an adhesive substrate 24. First, an adhesive sheath 26 is peeled to expose the adhesive substrate 24. Next using the description above for orientation, the instrument cleaner 2 is affixed to an operators 44 finger.

CONCLUSIONS, RAMIFICATIONS, AND SCOPE

Accordingly, the reader will see that the disposable finger mounted instrument cleaner can be used to clean instrumentation of debris with ergonomic efficiency. This can be accomplished with minimal disruption to procedural focus. The result is procedural seamlessness that promotes greater concentration and safety. In addition, the single use function of this swipe allows for instant disposal negating the need for time consuming and undesirable autoclaving. Moreover, additions of pressure sensitive and debris traps and pockets of the instrument cleaner for enhanced infection control and isolation of instrument-borne debris. Pressure sensitive grooves and pockets allow instrumentation heads to be enveloped and swiped clean, trapping debris within the foam body. The enveloping nature of the pressure grooves ensures that bio-residue will be safely contained within specific locations of the swipe. Furthermore, the DISPOSABLE FINGER MOUNTED INSTRUMENT CLEANER has additional advantages in that     It permits a variety of configurations for potentially demanding applications,     It can be pre-medicated with specialized antiseptics for fingertip access     Color-coded varieties can help distinguish specialized varieties.

Configurations can be made such that debris can be trapped sub-surface, greatly reducing the potential for exposing contaminants to undesirable surfaces.

Although the description above contained much specificity, these should not be construed as limiting the scope of the invention but merely as providing illustrations of some of the presently preferred embodiments of this invention. The disposable finger mounted instrument cleaner can assume any shape, size, or dimension that best allows for optimal cleaning of instruments. For example, the protective body may assume any shape and size as needed for optimal instrument cleaning. It may also be comprised of any material that promotes optimal security, stability and comfort. This includes all manners of synthetics, metals or other organic substances. Also, any number of specialized coatings may be applied to all exterior or interior aspects of the cleaner. This includes adhesives, infection control substances, or any other helpful substance.

The foam body may have any size, shape and thickness as needed for optimal instrument cleaning. Any viscosity of foam may be used. The foam may be layered. The foam may also be open or closed cell to ensure optimal collection absorption, compressibility, abrasiveness, stability, protection, and comfort. With regard to pressure grooves, any number may be present in any shape configuration necessary to best allow for swiping and debris collection effectiveness. Any number of internally located channels, appendages or debris traps may be incorporated to best enhance the collection and debris entrapment. Additionally, instrument cleaners designed for sharps or bladed instruments may have additional channels or pockets with slice resistant coatings or laminated layers of appropriately protective materials.

The instrument cleaner may also be used as a medicated delivery system for the purposes of infection control and/or introduction of therapeutic substances. The instrument cleaner may also be pre-medicated with any of these appropriate substances. Last, any of the above alternatives may be incorporated to any degree. Any features may be included or completely eliminated for optimal cleaning function.

Thus, the scope of the invention should be determined by the appended claims and their legal equivalents, rather than by the examples given.

We claim:

1. A finger mounted instrument cleaner comprising:
   (a) a circumferential protective ring to wrap around a finger, having a swiping expanse to occlude extensor and lateral aspects of a finger wherein said swiping expanse has an hour glass shaped flared region to correlate with lateral and flexor aspects of a finger;
   (b) a circumferential gripping coil to wrap around flexor aspects of a finger;
   (c) two instrument deflection guards flaring up from said protective ring; and
   (d) a foam body adherent to said swiping expanse wherein said foam body is dimensionally smaller than said swiping expanse.

2. The finger mounted instrument cleaner of claim 1 wherein said protective ring is a puncture resistant material.

3. The finger mounted instrument cleaner of claim 1 wherein said hour-glass shaped flared region has concavities or gripping grooves formed into its edges.

4. The finger mounted instrument cleaner of claim 1 wherein said foam body contains slits or pressure grooves within its face wherein said grooves run horizontally across said side and across said foam body's face.

5. A finger mounted instrument cleaner comprising:
   (a) a circumferential protective ring to wrap around a finger, having a swiping expanse to occlude extensor and lateral portions of a finger;
   (b) mirrored non-connective circumferential coils to wrap around flexor aspects of a finger;
   (c) two instrument deflection guards flaring up from said protective ring;
   (d) said swiping expanse having a hour glass shaped flared region to correlate with lateral and flexor aspects of a finger;
   (e) a foam body adherent to said swiping expanse wherein said foam body is dimensionally smaller than said swiping expanse; and
   (f) therein a pouch or pocket to permit insertion of an instrument head.

6. The finger mounted instrument cleaner of claim 5 wherein said hour-glass shaped flared region has concavities or gripping grooves formed into its edges.

7. The finger mounted instrument cleaner of claim 5 wherein said foam body contains slits or pressure grooves within its face wherein said grooves run horizontally across said side and across said foam body's face.

\* \* \* \* \*